(12) United States Patent
Favreau

(10) Patent No.: US 12,207,842 B2
(45) Date of Patent: Jan. 28, 2025

(54) ENDOSCOPIC ULTRASOUND GUIDED ACCESS NEEDLE

(71) Applicant: BOSTON SCIENTIFIC SCIMED, INC., Maple Grove, MN (US)

(72) Inventor: John Thomas Favreau, Charlton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/429,021

(22) Filed: Jan. 31, 2024

(65) Prior Publication Data

US 2024/0164806 A1 May 23, 2024

Related U.S. Application Data

(63) Continuation of application No. 17/247,018, filed on Nov. 24, 2020, now Pat. No. 11,925,386.

(60) Provisional application No. 62/944,725, filed on Dec. 6, 2019.

(51) Int. Cl.
*A61B 17/34* (2006.01)
*A61B 17/00* (2006.01)

(52) U.S. Cl.
CPC .... *A61B 17/3423* (2013.01); *A61B 17/00234* (2013.01); *A61B 17/3403* (2013.01); *A61B 2017/00296* (2013.01); *A61B 2017/0034* (2013.01); *A61B 2017/3413* (2013.01); *A61B 2017/3454* (2013.01)

(58) Field of Classification Search
CPC . A61B 17/34; A61B 17/3403; A61B 17/3454; A61B 17/3478; A61B 2017/3405; A61B 2017/3413
See application file for complete search history.

(56) References Cited

U.S. PATENT DOCUMENTS

| 4,808,170 | A | * | 2/1989 | Thornton | A61M 5/158 604/274 |
| 5,275,611 | A | * | 1/1994 | Behl | A61B 17/34 606/198 |
| 2016/0135842 | A1 | * | 5/2016 | Kassab | A61B 17/3496 604/117 |
| 2017/0224376 | A1 | * | 8/2017 | Kuracina | A61B 8/0841 |
| 2017/0296792 | A1 | * | 10/2017 | Ornelas Vargas | A61M 25/065 |

* cited by examiner

*Primary Examiner* — Nicholas W Woodall
(74) *Attorney, Agent, or Firm* — Fay Kaplun & Marcin, LLP

(57) ABSTRACT

An access needle includes a hollow shaft having a lumen sized and shaped to slidably receive a guidewire therein and having a distal end including an angled surface extending proximally and transversely from a sharpened distal-most tip of the shaft to a beveled smoothed area of the shaft proximal and transverse to the sharpened tip. The beveled smoothed area is positioned to slidably engage a guidewire extended distally out the distal end of the needle so that, as the guidewire is retracted proximally into the needle, the beveled smoothed area slidably engages the guidewire to minimize abrasion to the guidewire.

13 Claims, 6 Drawing Sheets

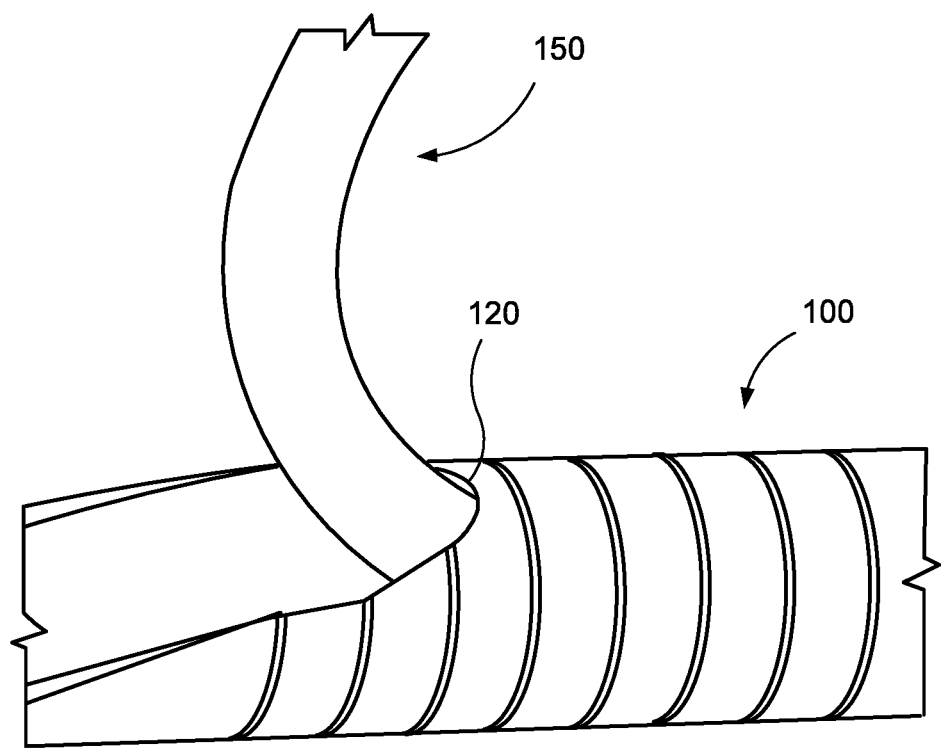
F I G. 10

ENDOSCOPIC ULTRASOUND GUIDED ACCESS NEEDLE

PRIORITY CLAIM

The present application is a Continuation of U.S. patent application Ser. No. 17/247,018 filed on Nov. 24, 2020, which claims priority to U.S. Provisional Patent Application Ser. No. 62/944,725 filed Dec. 6, 2019. The disclosures of the above application(s)/patent(s) are incorporated herewith by reference.

FIELD

The present disclosure relates to an endoscopic needle and, in particular, an endoscopic ultrasound (EUS) guided access needle.

BACKGROUND

A hollow needle may be used in an EUS-guided procedure to access target anatomy, e.g. an intestinal lumen, and introduce a guidewire through the needle lumen into the target anatomy to, e.g., guide a stenting procedure. The guidewire, when it is extended distally from the needle tip, may be bent in multiple directions and at different points such that, when the physician attempts to retract the guidewire into the needle, the guidewire may catch on the sharp edge or tip of the needle, potentially stripping the guidewire. The stripped material may be left behind in the anatomy and/or may expose the metal wire core of the guidewire and create an electrical safety hazard.

SUMMARY

The present disclosure relates to an access needle which includes a hollow shaft having a lumen sized and shaped to slidably receive a guidewire therein and having a distal end including an angled surface extending proximally and transversely from a sharpened distal-most tip of the shaft to a beveled smoothed area of the shaft proximal and transverse to the sharpened tip, the beveled smoothed area being positioned to slidably engage a guidewire extended distally out the distal end of the needle so that, as the guidewire is retracted proximally into the needle, the beveled smoothed area slidably engages the guidewire to minimize abrasion to the guidewire.

In an embodiment, the distal end of the shaft includes sharp cutting surfaces extending proximally from the sharpened tip, the beveled smoothed area being positioned so that, as a guidewire extending out of the distal end of the needle along a curve is retracted into the needle in a desired orientation relative to the needle, a surface of the guidewire which forms a radially inner surface along the curve contacts the beveled smoothed area of the needle.

In an embodiment, wherein the distal end of the shaft includes a first sharp cutting surface extending from the distal-most tip to a first transition and a second sharp cutting surface extending from the first transition to a second transition, the first sharp cutting surface extending at a first angle relative to a longitudinal plane of the shaft at the distal-most tip and curving to a second angle relative to the longitudinal plane of the shaft at the first transition, the second cutting surface having a third angle relative to the longitudinal plane of the shaft.

In an embodiment, the distal end of the shaft includes a third sharp cutting surface extending from the distal-most tip to a third transition and a fourth sharp cutting surface extending from the third transition to a fourth transition, the third sharp cutting surface extending at a fourth angle relative to a longitudinal plane of the shaft at the distal-most tip and curving to a fifth angle relative to the longitudinal plane of the shaft at the third transition, the fourth sharp cutting surface extending at a sixth angle relative to the longitudinal plane of the shaft.

In an embodiment, the first and second sharp cutting surfaces are substantially symmetric relative to a midplane of the needle with respect to the third and fourth sharp cutting surfaces.

In an embodiment, the first angle is in a first range of 0-10 degrees, the second angle is in a second range of 20-50 degrees and the third angle is in a third range of 10-30 degrees.

In an embodiment, the beveled smoothed area is defined by a U-shaped surface having a midpoint proximal and transverse to the sharpened tip, the U-shaped surface having a curvature at the midpoint parallel to a transverse plane of the shaft.

In an embodiment, the beveled smoothed area includes an outer bevel on an outer surface of the shaft and an inner bevel on an inner surface of the shaft.

In an embodiment, the shaft includes a feature extending along a distal portion thereof configured to mechanically engage a corresponding feature of a guidewire inserted therein to maintain the guidewire in a desired rotational orientation relative to the needle.

In an embodiment, the feature of the shaft includes a slot extending along a portion of a length of the needle configured to receive a tab extending radially from the guidewire.

The present disclosure also relates to an access needle assembly which includes an anchoring guidewire including a first orienting feature; and an access needle including a hollow shaft having a lumen sized and shaped to slidably receive the guidewire therein and having a distal end including a cut surface extending proximally and transversely from a sharpened distal-most tip of the shaft to a beveled smoothed area of the shaft proximal and transverse to the sharpened tip, the beveled smoothed area being positioned to slidably engage the guidewire extended distally out the distal end of the needle so that, as the guidewire is retracted proximally into the needle, the beveled smoothed area slidably engages the guidewire to minimize abrasion to the guidewire, the access needle further including a second orienting feature extending along a distal portion thereof configured to mechanically engage the first orienting feature to maintain the guidewire in a desired rotational orientation relative to the access needle.

In an embodiment, the second orienting feature includes a slot extending along a portion of a length of the needle and the first orienting feature includes a tab projecting outward from the guidewire.

In an embodiment, the tab has a ramped section to facilitate engagement of the shaft and the tab so that, when the needle is retracted proximally over the guidewire, the ramp engages a distal end of the slot so that the tab is folded over and passes through the needle until the tab has emerged from the distal end of the needle.

In an embodiment, the second orienting feature includes a slot extending along a portion of a length of the needle and the first orienting feature includes a tab projecting outward from the guidewire, the tab being configured to be severed from the guidewire as the needle is withdrawn proximally over the guidewire.

In an embodiment, the guidewire has a nitinol core with a polymer coating.

The present disclosure further relates to a method which includes extending a guidewire distally out of a distal end of an access needle, the access needle including a hollow shaft having a lumen sized and shaped to slidably receive the guidewire therein, the distal end of the needle including a cut surface extending proximally and transversely from a sharpened distal-most tip of the shaft to a beveled smoothed area of the shaft proximal and transverse to the sharpened tip; retracting the guidewire proximally back into the needle so that the beveled smoothed area slidably engages the guidewire to minimize abrasion to the guidewire.

In an embodiment, the method further includes rotating the guidewire relative to a longitudinal axis of the access needle to position a curve of the guidewire so that a portion of the guidewire surface forming a radially inner part of the curve contacts the beveled smooth area as the guidewire is retracted into the needle.

In an embodiment, the guidewire is rotated under ultrasound guidance so that the curved distal end curves away from a side of the needle on which the distal tip of the needle is formed.

In an embodiment, the distal end of the shaft includes sharp cutting surfaces extending proximally from the sharpened tip, the beveled smoothed area being positioned so that, as a guidewire extending out of the distal end of the needle along a curve is retracted into the needle in a desired orientation relative to the needle, a surface of the guidewire which forms a radially inner surface along the curve contacts the beveled smoothed area of the needle.

In an embodiment, the beveled smoothed area is defined by a U-shaped surface having a midpoint proximal and transverse to the sharpened tip, the U-shaped surface having a curvature at the midpoint parallel to a transverse plane of the shaft.

BRIEF DESCRIPTION OF THE DRAWINGS

FIG. 10 shows a side view of the access needle and guidewire of FIG. 7 where the guidewire engages the outer bevel of the access needle.

DETAILED DESCRIPTION

Figure 1:
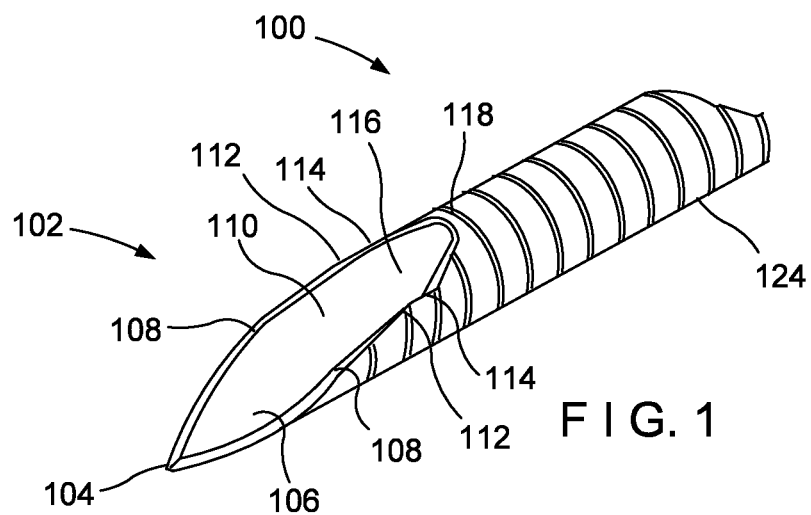
FIG. 1 shows an access needle having a distal end with a sharp distal tip for puncturing a target anatomy and a plurality of machined surfaces shaped for a smooth advancement and retraction of a guidewire.

The present disclosure may be further understood with reference to the following description and the appended drawings, wherein like elements are referred to with the same reference numerals. The exemplary embodiments describe devices having a needle with smoothed surfaces for ease of advancing or retracting a guidewire without damaging the guidewire. The exemplary devices may include means for aligning the guidewire within the needle so that the guidewire is caused to interact with the smoothly ground surfaces instead of sharper edges defined in the needle tip.

FIG. 1 shows a distal end of an access needle 100 having a distal end 102 with a sharp distal tip 104 for puncturing target anatomy and a plurality of machined surfaces shaped to facilitate smooth advancement and retraction of a guidewire 150 out of and back into the distal end 102. The needle 100 is formed as a hollow shaft 124 sized and shaped to slidably receive a guidewire 150 so that it may pass therethrough to be extended distally from the distal tip 102 as would be understood by those skilled in the art. The needle 100 may be formed from any suitable material, such as a nitinol alloy, a cobalt-chromium alloy, stainless steel, etc. The guidewire 150 may be configured to bend multiple times over a tortuous path which an insertion device such as an endoscope has traversed via, for example, a natural body lumen to access a target tissue structure. Additionally, the guidewire may be an anchoring guidewire having a shaped distal end that enables anchoring of tissue.

Figure 5:
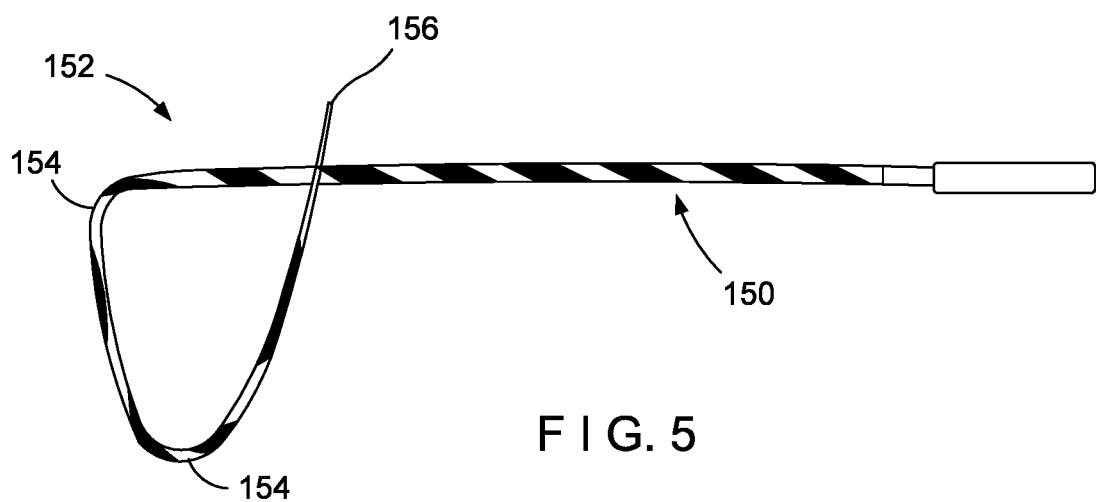
FIG. 5 shows an exemplary guidewire for use with the access needle of FIG. 1.

In the present embodiment, as shown in FIG. 5, the guidewire 150, in its unconstrained state, has a curved end 152 pre-formed to assume a curved shape having two curved sections 154, each curving through an angle of up to approximately ~135 degrees in the same curvature direction such that, when unconstrained, a distal tip 156 of the guidewire 150 points in a direction angled up to approximately ~270 degrees relative to the longitudinal axis of a portion of the guidewire 150 proximal to the curved end 152. However, guidewires having other curvatures may be used. As would be understood by those skilled in the art, the guidewire 150 is sufficiently flexible so that the curved end 152 can conform to the path along which the interior of the hollow shaft 124 extends when one or both of the curved sections 154 are withdrawn into the shaft 124. The guidewire 150 may have, for example, a nitinol core covered in a polymer coating.

When the curved end 152 of the wire 150 is extended distally out the distal tip 102 of the needle 100, i.e., when the curved end 152 is not constrained by the inner diameter of the shaft 124, the distal tip 156 of the guidewire 150 reverts to its unconstrained state. However, the guidewire 150 as described herein is used for exemplary purposes only, and any guidewire may be used with the access needle 100. For example, the guidewire may be curved at different points in different curvature directions and/or have more or fewer curves. Those skilled in the art will understand that guidewires with significant curvature at their distal ends are the most likely to be damaged upon withdrawal into a conventional needle as a radially inner side of the curved end is dragged over the sharp end of the needle to re-enter the lumen of the needle. As would be understood by those skilled in the art, guidewires with pre-formed curved distal ends are often used as anchoring guidewires. That is, this type of guidewire may be inserted into a target structure via a needle or other insertion device that holds the curved distal end substantially straight. Furthermore, the guidewire may be of any desired construction.

When the target structure has been accessed, the guidewire 150 may be advanced distally out of the needle 100 (or the needle 100 may be withdrawn proximally over the guidewire 150) to free the curved end 152 to assume its curved configuration. In this curved state, the guidewire 150 is no longer able to pass proximally out of the aperture through which it entered the target tissue structure and so is anchored within the target structure. The needle 100 may then be withdrawn proximally over the guidewire 150 which may then be used to provide a pathway for the insertion of other treatment devices (e.g., stents, etc.) over the guidewire 150 into the target structure.

When the procedure is completed, the needle 100 is again advanced distally over the guidewire 150 into the target structure. At this point, the guidewire 150 is withdrawn proximally into the needle 100 during which operation, contact between the walls of the lumen of the needle 100 and the guidewire 150 constrain the guidewire to return to the path of the lumen of the needle 100. The needle 100 with the guidewire received therein may then be withdrawn from the body. The needles of the present embodiments are directed to minimizing or eliminating damage to guidewires during their withdrawal proximally into the lumen of the needle.

Figure 2:
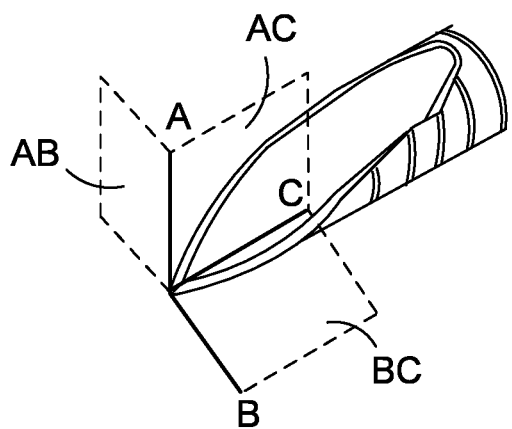
FIG. 2 shows the access needle of FIG. 1 with a needle coordinate system.

The opening at the distal end 102 of the needle 100 is defined by a plurality of machined surfaces cut into the hollow shaft 118. The opening is defined by a first segment 106, a second segment 110 and a third segment 116. The segments are defined in the manner described below, relative to a needle coordinate system with a longitudinal axis A, a first transverse axis B and a second transverse axis C, the axes defining a first longitudinal plane AC, a second longitudinal plane BC and a transverse plane AB, as shown in FIG. 2.

The distal end 102 has a sharp, tissue-penetrating, distal tip 104 at the origin of the needle coordinate system, i.e. the distal-most point of the access needle 100. In this embodiment, the opening at the distal end 102 of the needle 100 is substantially symmetrical with respect to the distal tip 104 so that the first, second and third segments on either side of the AC plane are mirror images of one another. The first segment 106 is defined by a first cut extending proximally and transversely from the distal tip 104 into the cylindrical wall of the needle 100.

Figure 8:
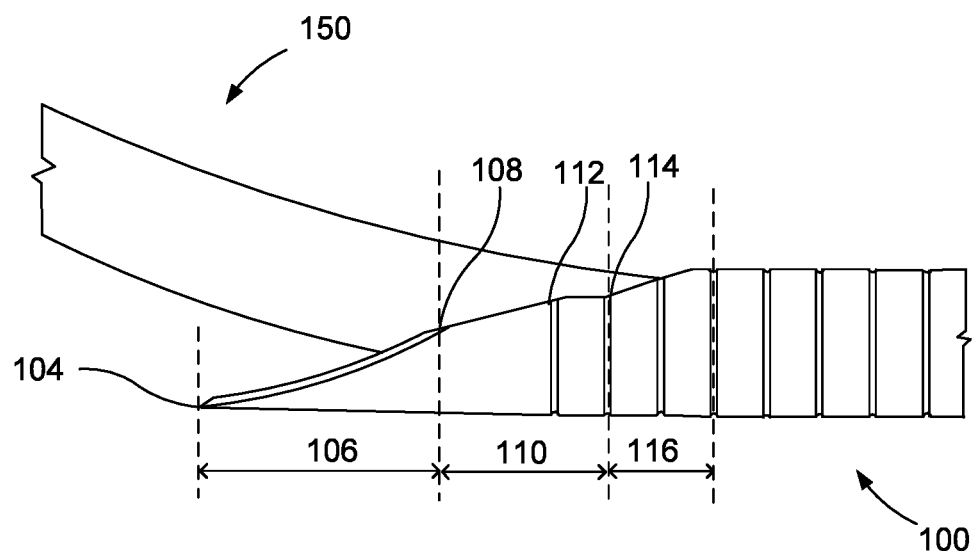
FIG. 8 shows a side view of the access needle and guidewire of FIG. 7 where the guidewire engages the inner bevel of the access needle.

The first cut begins at the distal tip 104 at a first angle relative to the BC plane, the first angle being between approximately 0 degrees and 10 degrees, i.e., substantially parallel or nearly parallel to the BC plane, and gradually steepens to a second angle relative to the BC plane at a first transition 108, as may be seen in FIG. 1 and more clearly in FIG. 8. For example, the second angle, i.e. the angle of the cut of the first segment 106 relative to the BC plane at the first transition 108, may be between approximately 20 degrees and 50 degrees. Thus, the first cut results in a curved first segment 106 that progresses from a shallow distal-most angle nearly parallel to a longitudinal axis of the needle 100 to a deeper angle relative to the longitudinal axis at the first transition 108. As noted above, the first cut of this embodiment is substantially symmetrical on both sides of the distal tip 104.

Figure 3:
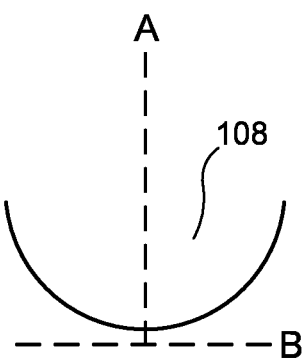
FIG. 3 shows a cross section of the distal end of the access needle of FIG. 1 at a first transition.
Figure 4:
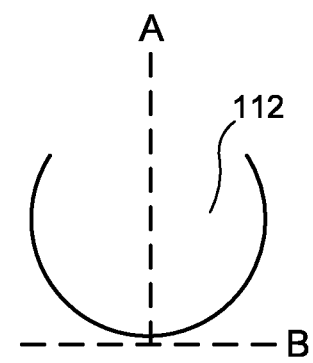
FIG. 4 shows a cross section of the distal end of the access needle of FIG. 1 at a second transition.

The second segment 110 is defined by a second cut extending proximally and transversely from the first transition 108 to a second transition 112 and a third cut extending only proximally, i.e., substantially parallel to the BC plane, from the second transition 112 to a third transition 114. The second cut is at a third angle relative to the BC plane, the third angle remaining substantially constant from the first transition 108 to the second transition 112. For example, the third angle, i.e. the angle of the second cut relative to the BC plane, may be between approximately 10 degrees and 30 degrees. It is noted that the second and third cuts are reflected on both sides of the needle 100. The cross section of the needle 100 at the first transition 108 is shown in FIG. 3, and the cross section of the needle 100 at the second transition 112 is shown in FIG. 4, which is the same as the cross section of the needle 100 at the third transition 114.

As those skilled in the art would understand, the first, second and third angles may differ from the exemplary angles provided above without departing from the scope of the invention. The shape of the first and second segments 106, 110 is configured for the puncturing and/or acquisition of tissue from a target site in a living body. Thus, the edges of the needle 100 resulting from the first, second and third cuts are left sharp.

The third segment 116 is defined by a fourth cut extending proximally and transversely from the third transition 114. The fourth cut is parallel to the A axis throughout the cut, with a varying angle relative to the AC plane, forming a substantially U-shaped cavity in the third segment 116. The fourth cut begins at the third transition 114 at a fourth angle relative to the AC plane, which may begin at approximately ~0 degrees, with the angle gradually increasing to ~90 degrees until the fourth cut reaches a midpoint 118, i.e. the furthest proximal point in the cut distal end 102. The angle of the fourth cut at the midpoint is substantially parallel to the AB plane and orthogonal to the AC plane. It is noted that the fourth cut is substantially symmetrical with respect to the AC plane. The fourth cut, in the absence of any further machining, would result in sharp edges on the inner and outer surfaces of the shaft 124.

During an endoscopic procedure, such as a procedure to insert a stent or a rendezvous procedure, a guidewire such as the guidewire 150 shown in FIG. 5 may be introduced into a target anatomical space and advanced distally out of the needle 100. This allows the guidewire 150 to revert to its unconstrained bent configuration anchoring it in the target space. After the procedure has been completed and it is desired to withdraw the guidewire 150 from the body, the user inserts the needle 100 over the guidewire 150 until the distal tip 104 of the needle 100 enters the target space. The user then withdraw the curved end 152 of the guidewire 150 proximally back into the distal end 102 of the needle 100. As indicated above, if the guidewire 150 was drawn back into the needle 100 in such a manner that the guidewire 150 was dragged over a sharp tissue cutting surface the guidewire 150 may be damaged.

Figure 6:
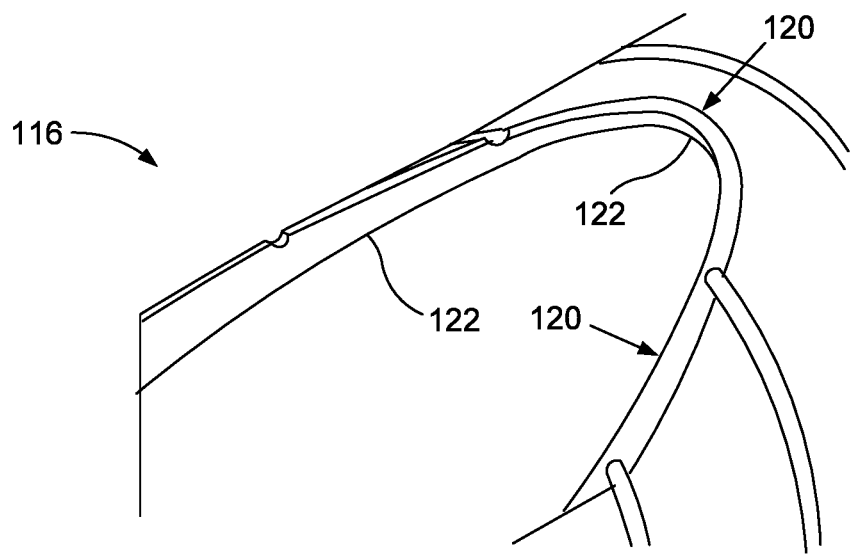
FIG. 6 shows a beveled portion of the distal end of the access needle of FIG. 1.

To mitigate the aforementioned risk, in an exemplary embodiment the needle 100 is machined further after the first, second, third and fourth cuts are made. As shown in FIG. 6, the distal end 102 has an outer bevel 120, smoothing the sharp edge on the outer surface of the third segment 116, and an inner bevel 122, smoothing the sharp edge on the inner surface of the third segment 116 to minimize the effects of contact between these surfaces and the guidewire 150. A radius of curvature for both the outer bevel 120 and the inner bevel 122 may range from approximately 0" to 0.010". Furthermore, the outer bevel 120 and the inner bevel 122 each has a degree of curvature of approximately 45 degrees to avoid creating a new sharp edge. In another embodiment, the outer and inner bevel 120, 122 may be an outer radius and inner radius, an outer chamfer and inner chamfer, or an outer fillet and an inner fillet. Moreover, the third segment 116 may have a combination of a bevel, radius, chamfer, and fillet (e.g. the sharp edge of the outer surface is a fillet and the sharp edge of the inner surface is a bevel).

Figure 7:
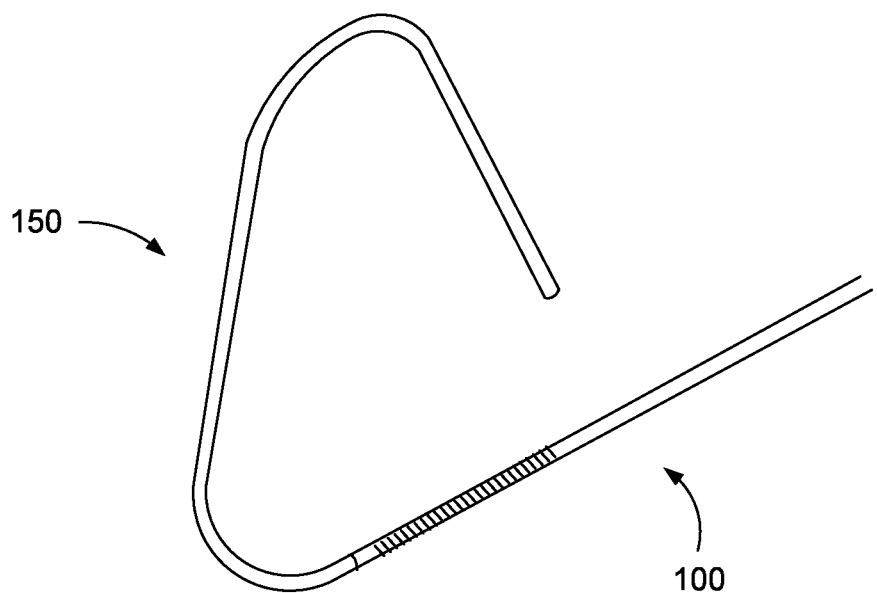
FIG. 7 shows the access needle of FIG. 1 with the exemplary guidewire of FIG. 5 extended therefrom.
Figure 9:
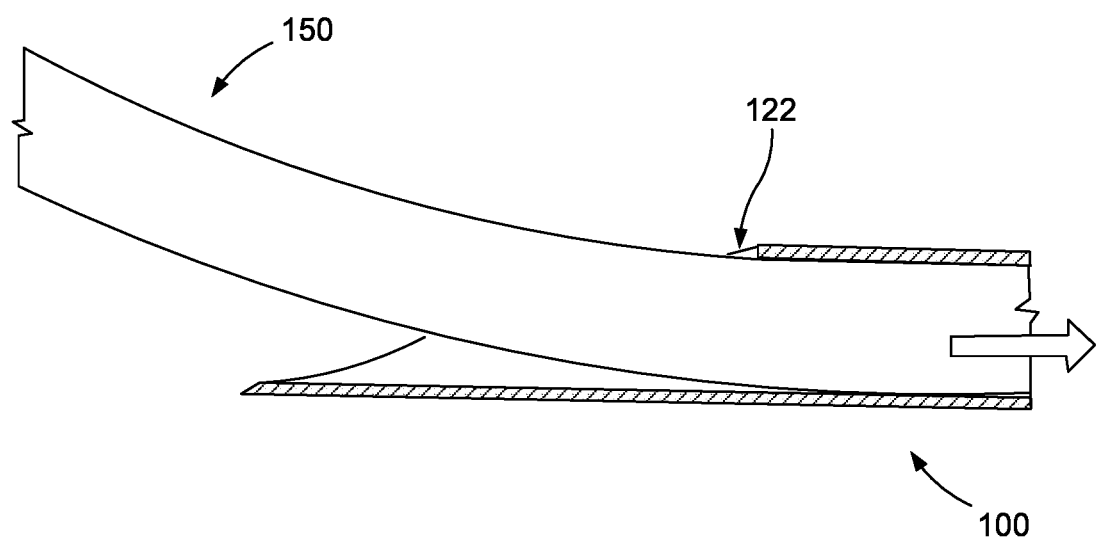
FIG. 9 shows a section view of the access needle and guidewire of FIG. 8.

FIG. 7 shows the needle 100 of FIG. 1 with the guidewire 150, the curved end 152 of the guidewire 150, extending distally out the distal end 102. FIGS. 8-10 show an exemplary interaction of the guidewire 150 with the distal end 102 during retraction thereof. The guidewire 150 in this embodiment is curved around the B axis of the needle, ensuring that, as the guidewire 150 is withdrawn into the needle 100, it is drawn across the surface defined in the third segment 116 of the distal end 102 and not over the sharper surfaces of the first and second segments 106, 110, respectively. As may be seen in FIG. 9, the guidewire 150 is drawn over the smoothed inner bevel 122, thus mitigating the risk of the guidewire 150 being stripped during the retraction. As may be seen in FIG. 10, when the radius of curvature of the guidewire 150 is small, the interaction between the guidewire 150 and the bevels 120, 122 increases, such that the guidewire 150 may also be drawn over the outer bevel 120.

To bring a guidewire into contact only with beveled third segment 116, rather than the sharp first or second segments 106, 110, it must be ensured that the guidewire is properly aligned rotationally within the needle 100. In other words, the curvature of the guidewire 150 during retraction must be oriented so that the curvature of the guidewire 150 extends generally within the AC plane and the guidewire 150 curves away from the side of the needle 100 on which the distal tip 104 is formed. If a guidewire has a more complex curvature (e.g., a curvature extending in more than one plane), the user may rotate the guidewire 150 or the needle 100 relative to the other under Ultrasonic visualization so that the segment that is currently entering the needle 100 is oriented in the AC plane as described above. Thus, the guidewire 150 will always contact the third segment 116 as it enters the needle 100.

The needle 100 and the guidewire 150 may have features for enhancing their visualization under ultrasound guidance, such that the operating physician may ensure that the proper alignment of the needle 100 and guidewire 150 is achieved by monitoring the orientations of the elements. For example, the needle 100 and the guidewire 150 may be formed from echogenic materials. However, it is possible that retraction may occur without direct visualization. Thus, proper alignment of the elements may be ensured in an alternate manner.

Figure 11:
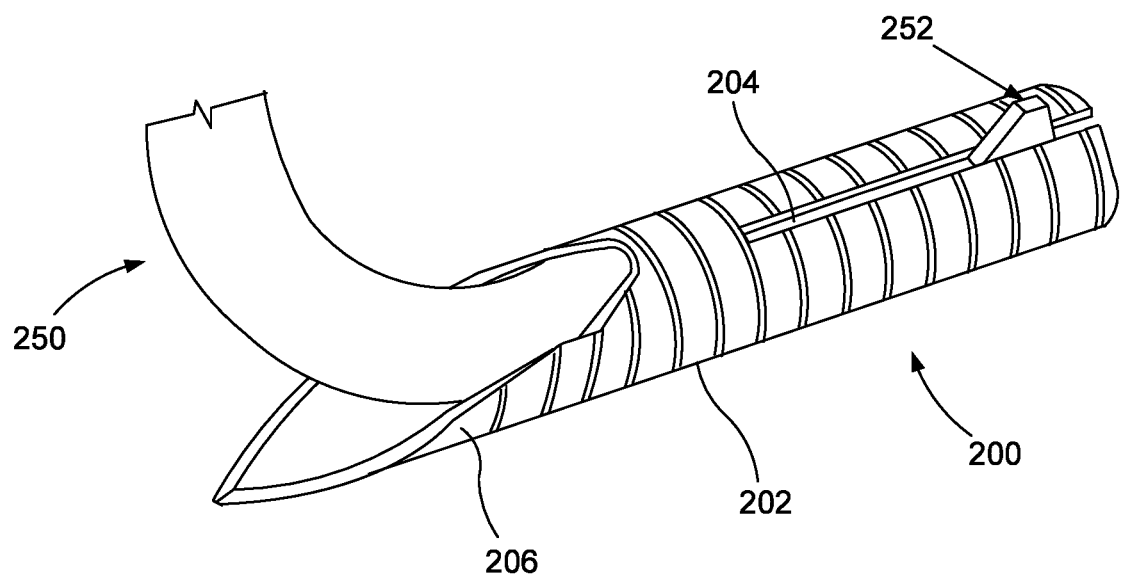
FIG. 11 shows an access needle with a longitudinal slot and a guidewire with an alignment tab according to a second exemplary embodiment.
Figure 12:
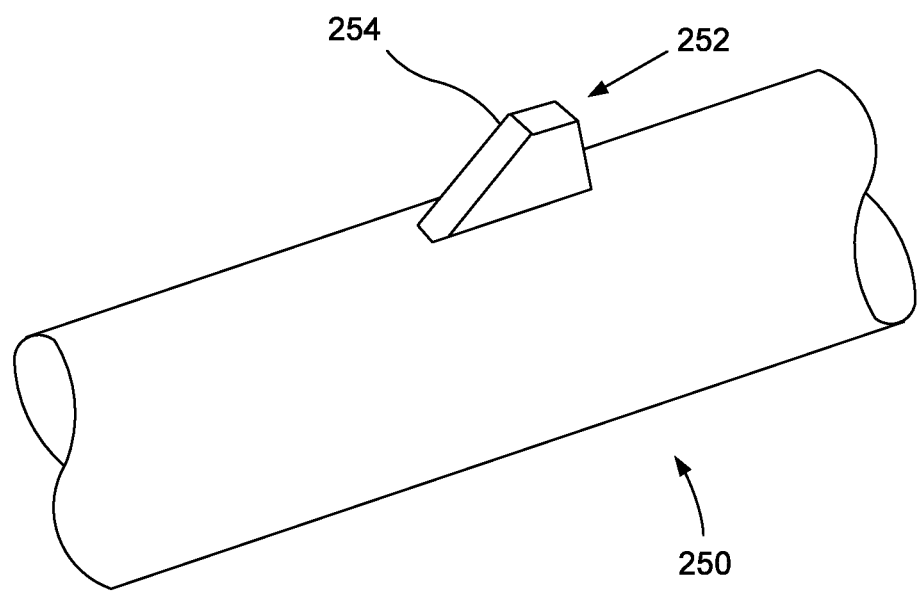
FIG. 12 shows a slanted edge of the alignment tab of FIG. 11.

FIGS. 11-12 show an access needle 200 having a longitudinal slot 204 in its hollow shaft 202. The access needle 200 may be used in conjunction with a guidewire 250 having a tab 252 projecting radially outward (e.g., welded or coated onto the wire 250) that is sized and shaped to travel in the longitudinal slot 204 during distal advancement and proximal retraction of the guidewire 250 out of and into the needle 200. The tab 252 is restricted from transverse motion by the slot 204. In other words, interaction between the tab 252 and the slot 204 maintains the guidewire 250 in a selected rotational alignment relative to the access needle 200 throughout the procedure.

The slot 204, in this embodiment, is closed at a distal end 206 of the needle 200. However, in another embodiment, the slot 204 may be open at the distal end 206. Thus, it may be ensured that the curvature of the guidewire 250 interacts only with the beveled portions of the needle 200. Those skilled in the art will understand that this slot may be curved in a manner corresponding to the curvature of more complex guidewire shapes to ensure that a distal end of the guidewire 250 rotates into the desired alignment relative to the needle 200 at all times during the withdrawal of the guidewire 250 into the needle 200.

In some procedures, the needle 200 is pulled proximally off the guidewire 250 after the guidewire 250 has been anchored in the target anatomy. The existence of the tab 252 could prevent such a withdrawal of the needle 200 if it is not designed to allow the needle 200 to pass thereover. As would be understood by those skilled in the art, the tab 252 may be designed so that it will snap off as the needle 200 is pulled proximally off the guidewire 250. In another embodiment, the tab 252 may be designed to compress and pass through the distal end of the lumen of the needle 200 until it exits the distal end 206 of the needle 200. The needle 200 may then be slid proximally off of the guidewire 250 and removed from the body. For example, the tab 252 may have a ramped section 254 that facilitates the folding over of a leading edge of the tab 252 as it reaches the distal end of the slot 204 so that the tab 252 folds over and is compressed into the lumen of the needle 200 as the tab 252 passes under the portion of the needle 200 distal to the distal end of the slot 204 as the needle 200 is drawn proximally over the guidewire 250.

Figure 13:
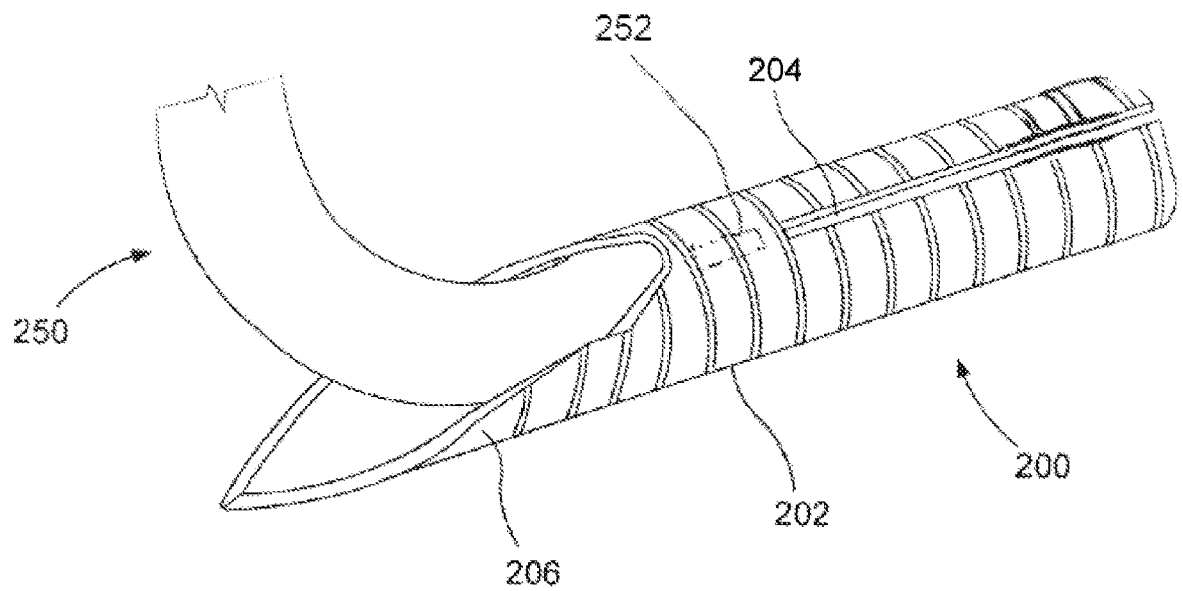
FIG. 13 shows an access needle where the alignment tab of the guidewire is folded over and compressed into lumen of the needle until the tab emerges from the distal end of the needle.
Figure 14:
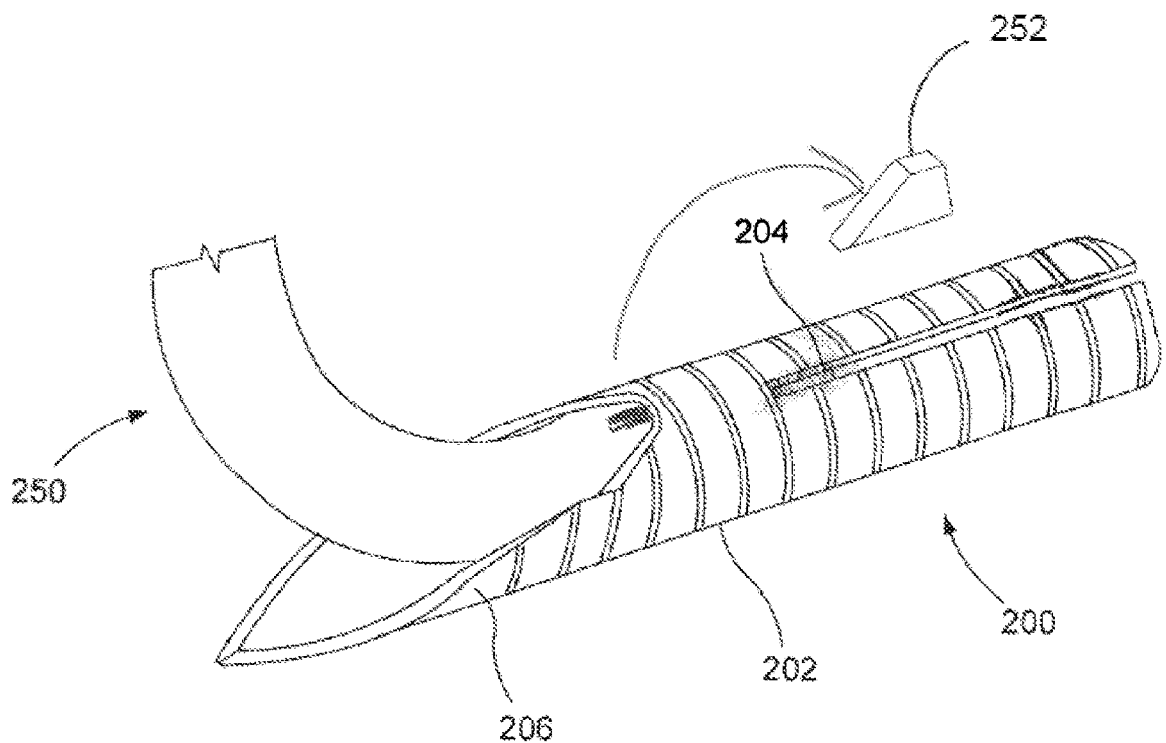
FIG. 14 shows an access needle where the alignment tab is severed from the guidewire as the needle is withdrawn proximally over the guidewire.

FIG. 13 shows an access needle 200 having a tab 252 with a ramped section 254 which facilitates engagement of the shaft and the tab 252 so that, when the needle is retracted proximally over the guidewire, the ramp 254 engages a distal end of the slot 204 so that the tab 252 folds over and passes through the lumen of the access needle 200 until the tab has emerged from the distal end of the access needle 200. FIG. 14 shows an access needle 200 pulled proximally over a guidewire having a tab 252 which has been severed from the guidewire as a result of the access needle 200 being withdrawn proximally over the guidewire.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiment disclosed, but rather modifications are also covered within the scope of the present invention as defined by the appended claims.

The invention claimed is:

1. A method, comprising:
extending a guidewire distally out of a distal end of an access needle, the access needle including a hollow shaft having a lumen sized and shaped to slidably receive the guidewire therein, the distal end of the needle including a cut surface extending proximally and transversely from a sharpened distal-most tip of the shaft to a beveled smoothed area of the shaft proximal and transverse to the sharpened tip; and
retracting the guidewire proximally back into the needle so that the beveled smoothed area slidably engages the guidewire to minimize abrasion to the guidewire.

2. The method of claim 1, further comprising:
rotating the guidewire relative to a longitudinal axis of the access needle to position a curve of the guidewire so that a portion of a guidewire surface forming a radially inner part of the curve contacts the beveled smooth area as the guidewire is retracted into the needle.

3. The method of claim 2, wherein the guidewire is rotated under ultrasound guidance so that the curved distal end curves away from a side of the needle on which the distal tip of the needle is formed.

4. The method of claim 1, wherein the distal end of the shaft includes sharp cutting surfaces extending proximally from the sharpened tip, the beveled smoothed area being positioned so that, as the guidewire extending out of the distal end of the needle along a curve is retracted into the needle in a desired orientation relative to the needle, a surface of the guidewire which forms a radially inner surface along the curve contacts the beveled smoothed area of the needle.

5. The method of claim 4, wherein the beveled smoothed area is defined by a U-shaped surface having a midpoint proximal and transverse to the sharpened tip, the U-shaped surface having a curvature at the midpoint parallel to a transverse plane of the shaft.

6. The method of claim 1, wherein the distal end of the shaft includes a first sharp cutting surface extending from the distal-most tip to a first transition and a second sharp cutting surface extending from the first transition to a second transition, the first sharp cutting surface extending at a first angle relative to a longitudinal plane of the shaft at the distal-most tip and curving to a second angle relative to the longitudinal plane of the shaft at the first transition, the second sharp cutting surface having a third angle relative to the longitudinal plane of the shaft.

7. The method of claim 6, wherein the distal end of the shaft includes a third sharp cutting surface extending from the distal-most tip to a third transition and a fourth sharp cutting surface extending from the third transition to a fourth transition, the third sharp cutting surface extending at a fourth angle relative to a longitudinal plane of the shaft at the distal-most tip and curving to a fifth angle relative to the longitudinal plane of the shaft at the third transition, the fourth sharp cutting surface extending at a sixth angle relative to the longitudinal plane of the shaft.

8. The method of claim 7, wherein the first and second sharp cutting surfaces are substantially symmetric relative to a midplane of the needle with respect to the third and fourth sharp cutting surfaces.

9. The method of claim 6, wherein the first angle is in a first range of 0-10 degrees, the second angle is in a second range of 20-50 degrees and the third angle is in a third range of 10-30 degrees.

10. The method of claim 1, wherein the beveled smoothed area includes an outer bevel on an outer surface of the shaft and an inner bevel on an inner surface of the shaft.

11. The method of claim 1, wherein the shaft is formed from one of a nitinol alloy, a cobalt-chromium alloy and stainless steel.

12. The method of claim 1, wherein the shaft includes a feature extending along a distal portion thereof configured to mechanically engage a corresponding feature of the guidewire inserted therein to maintain the guidewire in a desired rotational orientation relative to the needle.

13. The method of claim 12, wherein the feature of the shaft includes a slot extending along a portion of a length of the needle configured to receive a tab extending radially from the guidewire.

* * * * *